(12) United States Patent
Cox et al.

(10) Patent No.: US 10,322,113 B2
(45) Date of Patent: Jun. 18, 2019

(54) PHARMACEUTICAL COMPOSITIONS DIRECTLY TARGETING FKBP52 FOR THE TREATMENT OF PROSTATE CANCER AND METHODS OF USING SAME

(71) Applicants: Marc Cox, El Paso, TX (US); Artem Cherkasov, El Paso, TX (US)

(72) Inventors: Marc Cox, El Paso, TX (US); Artem Cherkasov, El Paso, TX (US)

(73) Assignees: THE BOARD OF REGENTS OF THE UNIVERSITY OF TEXAS SYSTEM, Austin, TX (US); THE UNIVERSITY OF BRITISH COLUMBIA, Vancouver, BC (CA)

( * ) Notice: Subject to any disclaimer, the term of this patent is extended or adjusted under 35 U.S.C. 154(b) by 0 days.

(21) Appl. No.: 15/504,562

(22) PCT Filed: Aug. 20, 2015

(86) PCT No.: PCT/US2015/046187
§ 371 (c)(1),
(2) Date: Feb. 16, 2017

(87) PCT Pub. No.: WO2016/029068
PCT Pub. Date: Feb. 25, 2016

(65) Prior Publication Data
US 2017/0231964 A1     Aug. 17, 2017

Related U.S. Application Data

(60) Provisional application No. 62/039,712, filed on Aug. 20, 2014.

(51) Int. Cl.
C07D 235/28     (2006.01)
A61K 31/4184    (2006.01)
A61K 45/06      (2006.01)

(52) U.S. Cl.
CPC .......... *A61K 31/4184* (2013.01); *A61K 45/06* (2013.01); *C07D 235/28* (2013.01)

(58) Field of Classification Search
None
See application file for complete search history.

(56) References Cited

U.S. PATENT DOCUMENTS

| | | | |
|---|---|---|---|
| 2006/0147914 A1 | 7/2006 | Worley | 435/325 |
| 2006/0269950 A1 | 11/2006 | Kilbourne | 435/6.14 |
| 2010/0063099 A1 | 3/2010 | Levin | 514/338 |
| 2010/0168203 A1 | 7/2010 | Levin | 514/44 A |
| 2012/0283215 A1 | 11/2012 | Neckers | 514/61 |

OTHER PUBLICATIONS

STN Registry entry for CAS RN 342397-55-1, Entered STN Jun. 19, 2001, Accessed Nov. 8, 2018.*
Cheung-Flynn et al., *Mol. Endocrinol.*, 19:1654-66 (2005).
De Leon et. al. 2011. *PNAS.* 108(29): 11878-83.
Estebanez-Perpina et al., *Proc. Natl. Acad. Sci. USA*, 104:16074-79 (2007).
International Preliminary Report on Patentability in International Application No. PCT/US2015/046187 dated Mar. 2, 2017.
Riggs et al., *EMBO J.*, 22:1158-67 (2003).
Search Report and Written Opinion in International No. PCT/US2015/046187 dated Nov. 24, 2015.
Tranguch et al., *J. Clin. Invest.*, 117:1824-34 (2007).

* cited by examiner

*Primary Examiner* — Alicia L Otton
(74) *Attorney, Agent, or Firm* — Norton Rose Fulbright US LLP

(57) ABSTRACT

Embodiments of the current invention include methods and compositions for regulating the activity of hormone receptors.

4 Claims, 18 Drawing Sheets

PHARMACEUTICAL COMPOSITIONS DIRECTLY TARGETING FKBP52 FOR THE TREATMENT OF PROSTATE CANCER AND METHODS OF USING SAME

This application is a national phase application under 35 U.S.C. § 371 of International Application No. PCT/US2015/046187, filed Aug. 20, 2015 which claims priority to U.S. Provisional Patent Application Ser. No. 62/039,712 filed Aug. 20, 2014 Both applications are hereby incorporated in their entirety.

STATEMENT REGARDING FEDERALLY FUNDED RESEARCH

This invention as made with government support under Grant Nos. GM084863 and MD007592 awarded by the National Institutes of Health. The government has certain rights in the invention.

BACKGROUND

Steroid hormone receptors, including androgen receptor (AR), glucocorticoid receptor (GR), and the progesterone receptor (PR), require the ordered assembly of various chaperone and co-chaperone proteins in order to reach a functional state. The final stage in the receptor maturation process requires the formation of a multimeric complex consisting of an Hsp90 dimer, p23, and one of several large immunophilins. Previous studies have demonstrated that (i) the large immunophilin, FK506-binding protein 52 (FKBP52), acts to potentiate GR, AR, and PR receptor signaling pathways, and (ii) FKBP52-mediated regulation of receptor function appears to be localized to the receptor hormone binding domain. In cellular studies, FKBP52 has been shown to preferentially regulate GR, AR, and PR receptor-mediated signal transduction. See, for example, Cheung-Flynn et al., *Mol. Endocrinol.*, 19:1654-66 (2005); Riggs et al., *EMBO J.*, 22:1158-67 (2003); and Tranguch et al., *J. Clin. Invest.*, 117:1824-34 (2007). Given its receptor specificity, FKBP52 represents an attractive therapeutic target for the treatment of hormone-dependent diseases.

To date, the only known compounds for inhibition of AR function are related to selective AR modulators that bind to the hormone binding pocket, and are therefore competitive inhibitors of endogenous hormone binding. It has been shown that when certain molecules bind to the BF3 region of the AR hormone binding domain they can generally inhibit AR function in the 100 µM range. See, Estebanez-Perpina et al., *Proc. Arad Acad. Sci. USA*, 104:16074-79 (2007). However, there still exists a need for compounds which are selective AR modulators which are not competitive agonists or antagonists to endogenous hormone binding.

Androgens are a major stimulator of prostate tumor growth and all current therapies act as classic antagonists by competing with androgens for binding the AR hormone binding pocket. This mechanism of action exploits the dependence of AR for hormone activation and current treatment options are essentially ineffective once androgen-dependence is lost.

Thus, the direct targeting of FKBP52 with small molecules will lead to a more potent drug with the potential to simultaneously hit a variety of targets known to have, or suspected of having, a role in prostate cancer.

SUMMARY

Certain embodiments are directed to therapeutic methods comprising administering an effective amount of GMC1 (Formula I) to a patient in need thereof

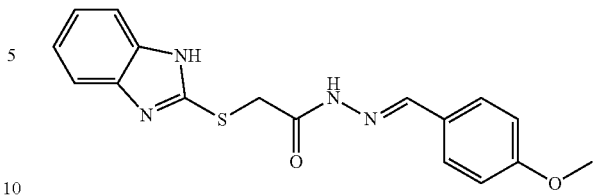

Formula I (GMC1)

In certain aspects a patient is identified as having a disorder or condition related to activation of androgen receptor (AR), progesterone receptor (PR), or glucocorticoid receptor (GR). In a further aspect the patient is a cancer patient. In certain aspects the cancer is a hormone dependent cancer. The hormone dependent cancer can be prostate cancer or prostate hypertrophy.

Certain embodiments are directed to compositions and methods of use for a compound having a chemical structure of Formula II

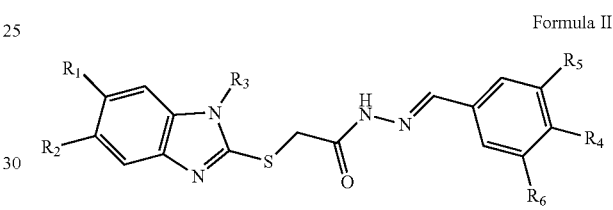

Formula II wherein R1 or R2 is independently and separately selected from H, amino, nitro, halogen, F5S, F3C, or C1-C3 alkoxy; R3 is independently selected from H or C1-C3 alkyl; R4 is independently selected from H, C1-C3 alkyl, C1-C3 alkoxy, or hydroxyl; R5 is independently selected from H, halogen, or C1-C3 alkoxy; and R6 is independently selected from H, halogen, hydroxyl, C1-C3 alkoxy. In certain aspects the halogen is F, Cl, or I.

In certain aspects, $R_1$ is independently selected from amino, nitro, halogen, $F_5S$, $F_3C$, or C1-C3 alkoxy; $R_2$ is selected from H or halogen; $R_4$ is methoxy (—$OCH_3$); and $R_3$, $R_5$, and $R_6$ are hydrogen. In certain aspect $R_1$ and/or $R_2$ halogen is independently F, Cl, or I. Various examples of these compounds are provided in FIG. 7A.

In certain aspects, $R_1$ is independently selected from amino, nitro, halogen, $F_5S$, $F_3C$, or C1-C3 alkoxy; $R_2$ is selected from H or halogen; $R_3$ is methyl; $R_4$ is methoxy (—$OCH_3$); and $R_5$ and $R_6$ are hydrogen. In certain aspect the $R_1$ and/or $R_2$ halogen is independently F, Cl, or I. Various examples of these compounds are provided in FIG. 7B.

In certain aspects, $R_1$ is independently selected from amino, nitro, halogen, $F_5S$, $F_3C$, or C1-C3 alkoxy; $R_2$ is selected from H or halogen; $R_4$ is hydroxy; and $R_3$, $R_5$, and $R_6$ are hydrogen. In certain aspect the $R_1$ and/or $R_2$ halogen is independently F, Cl, or I. Various examples of these compounds are provided in FIG. 7C.

In certain aspects, $R_1$ is independently selected from amino, nitro, halogen, $F_5S$, $F_3C$, or C1-C3 alkoxy; $R_2$ is selected from H or halogen; $R_4$ and $R_5$ are methoxy (—$OCH_3$); and $R_3$ and $R_6$ are hydrogen. In certain aspect the $R_1$ and/or $R_2$ halogen is independently F, Cl, or I. Various examples of these compounds are provided in FIG. 7D.

In certain aspects, $R_1$ is independently selected from amino, nitro, halogen, $F_5S$, $F_3C$, or C1-C3 alkoxy; $R_2$ is selected from H or halogen; $R_4$, $R_5$, and $R_6$ are methoxy (—$OCH_3$); and $R_3$ is hydrogen. In certain aspect the $R_1$ and/or $R_2$ halogen is independently F, Cl, or I. Various examples of these compounds are provided in FIG. 7E.

In certain aspects, $R_1$ is independently selected from amino, nitro, halogen, $F_5S$, $F_3C$, or C1-C3 alkoxy; $R_2$ is selected from H or halogen; $R_4$ is methoxy (—$OCH_3$); $R_6$ is hydroxyl; and $R_3$ and $R_5$ are hydrogen. In certain aspect the $R_1$ and/or $R_2$ halogen is independently F, Cl, or I. Various examples of these compounds are provided in FIG. 7F.

In certain aspects, $R_1$ is independently selected from amino, nitro, halogen, $F_5S$, $F_3C$, or C1-C3 alkoxy; $R_2$ is selected from H or halogen; $R_4$ is methoxy (—$OCH_3$); $R_6$ is Cl; and R3 and $R_5$ are hydrogen. In certain aspect the $R_1$ and/or $R_2$ halogen is independently F, Cl, or I. Various examples of these compounds are provided in FIG. 7G.

In certain aspects, $R_1$ is independently selected from amino, nitro, halogen, $F_5S$, $F_3C$, or C1-C3 alkoxy; $R_2$ is selected from H or halogen; $R_4$ is methoxy (—$OCH_3$); $R_6$ is Br; and $R_3$ and $R_5$ are hydrogen. In certain aspect the $R_1$ and/or $R_2$ halogen is independently F, Cl, or I. Various examples of these compounds are provided in FIG. 7H.

In certain aspects, $R_1$ is independently selected from amino, nitro, halogen, $F_5S$, $F_3C$, or C1-C3 alkoxy; $R_2$ is selected from H or halogen; $R_4$ is methoxy (—$OCH_3$); $R_6$ is I; and $R_3$ and $R_5$ are hydrogen. In certain aspect the $R_1$ and/or $R_2$ halogen is independently F, Cl, or I. Various examples of these compounds are provided in FIG. 7I.

In certain aspects, $R_1$ is independently selected from amino, nitro, halogen, $F_5S$, $F_3C$, or C1-C3 alkoxy; $R_2$ is selected from H or halogen; $R_4$ is methoxy (—$OCH_3$); $R_5$ and $R_6$ are F; and $R_3$ is hydrogen. In certain aspect $R_1$ and/or $R_2$ halogen is independently F, Cl, or I. Various examples of these compounds are provided in FIG. 7J.

In certain aspects, $R_1$ is independently selected from amino, nitro, halogen, $F_5S$, $F_3C$, or C1-C3 alkoxy; $R_2$ is selected from H or halogen; $R_4$ and $R_5$ are methoxy (—$OCH_3$); $R_6$ is Br; and $R_3$ is hydrogen. In certain aspect the $R_1$ and/or $R_2$ halogen is independently F, Cl, or I. Various examples of these compounds are provided in FIG. 7K.

In certain aspects, $R_1$ is independently selected from amino, nitro, halogen, $F_5S$, $F_3C$, or C1-C3 alkoxy; $R_2$ is selected from H or halogen; $R_4$ is methoxy (—$OCH_3$); $R_6$ is F; and $R_3$ and $R_5$ are hydrogen. In certain aspect the $R_1$ and/or $R_2$ halogen is independently F, Cl, or I. Various examples of these compounds are provided in FIG. 7L.

Other embodiments are directed to any of the compounds illustrated in FIG. 7A to 7L.

Certain embodiments are directed to therapeutic methods comprising administering an effective amount of the above described GMC1 analogs or derivatives to a patient in need thereof. In certain aspects the patient has prostate cancer. In a further aspect the compound is administered in combination with known prostate cancer therapies.

As used herein, the term "IC50" refers to an inhibitory dose that results in 50% of the maximum response obtained.

The term half maximal effective concentration (EC50) refers to the concentration of a drug that presents a response halfway between the baseline and maximum after some specified exposure time.

The terms "inhibiting," "reducing," or "prevention," or any variation of these terms, when used in the claims and/or the specification includes any measurable decrease or complete inhibition to achieve a desired result.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "patient" or "subject" refers to a living mammalian organism, such as a human, monkey, cow, sheep, goat, dogs, cat, mouse, rat, guinea pig, or species thereof.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
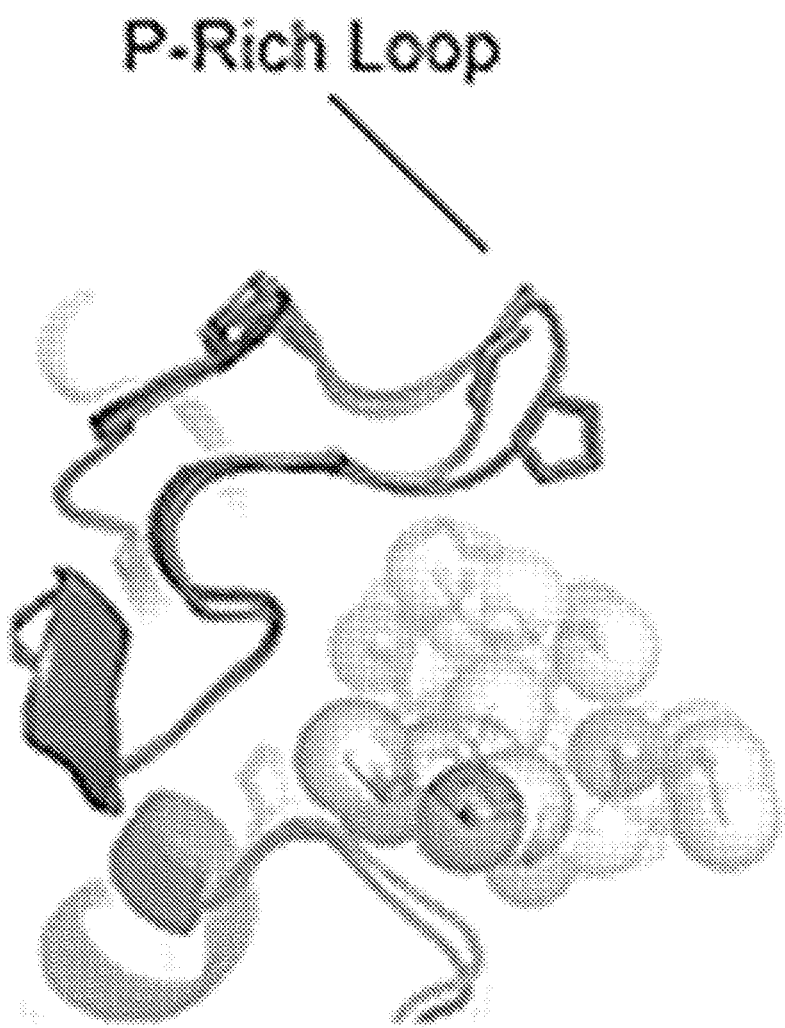
FIG. 1. Ligand-induced reorientation of the FKBP12 proline-rich loop. The apo FKBP12 structure (PDB ID 1FKK) superimposed onto the FK506 bound structure (PDB ID 1FKJ) by pair-wise alignment program DaliLite. Proline 88 (right) and 93 (left) are shown in sticks. FK506 is shown in sticks with spacefill. Note that docking of the FK506 ligand reorients the proline-rich loop providing precedence for molecule docking in the PPlase pocket of FKBP52 to disrupt proline-rich loop interactions.

Both FKBP52 and β-catenin have emerged in recent years as attractive therapeutic targets. Previous patents describe MJC13, which represents a first-in-class drug for targeting the regulation of AR by FKBP52. Through binding a recently identified regulatory surface on AR (BF3), MJC13 prevents the FKBP52-receptor complex from dissociating resulting in the retention of AR in the cytoplasm. MJC13 was shown to effectively block AR signaling and AR-dependent cancer cell proliferation in a variety of human prostate cancer cell lines, and preliminary preclinical studies demonstrate impressive effects on tumor growth in a prostate cancer xenograft model.

FKBP52 PPlase activity is important for FKBP52 regulation of abnormal Tau protein aggregation and other roles in the brain. Although, PPlase activity is not required for FKBP52 regulation of steroid hormone receptor activity. Thus, a molecule that binds the PPlase pocket and inhibits PPlase activity is not automatically assumed to inhibit FKBP52 regulation of receptor activity. Given that many of the identified molecules are predicted to bind the PPlase pocket with high affinity, but do not inhibit FKBP52 regulation of receptor activity, lends support to this idea. PPlase pocket binding molecules have not been disclosed with the sole purpose of inhibiting steroid hormone receptor activity. In addition, the labs that have pursued PPlase inhibitors have not assessed them for the ability to inhibit receptor activity. Certain embodiments are directed to identifying a molecule that, when docked in the PPlase pocket, could disrupt proline-rich loop conformation and interactions.

While the targeting of the FKBP52 regulatory surface on AR is a promising therapeutic strategy that allows for AR-specific targeting, the direct targeting of FKBP52 offers a number of advantages over MJC13 that would lead to a more potent and effective drug. First, the AR BF3 surface represents a less than ideal drug binding site, and, as a result, effective drug concentrations are achievable in the low micromolar range. In contrast, the FKBP52 PPlase pocket not only represents an ideal hydrophobic drug binding pocket, but the FKBP PPlase pocket is a known 'druggable target' as the immunosuppressive drug Tacrolimus is already FDA approved for use in the clinic. Also, given the conservation within the FKBP PPlase pocket, drugs targeting the FKBP52 PPlase pocket would likely target FKBP52 and the closely related FKBP51 protein simultaneously. While FKBP52, but not FKBP51, is largely considered the relevant steroid hormone receptor regulator, more recent evidence suggests that both FKBP51 and FKBP52 are positive regulators of AR in prostate cancer cells. In addition, FKBP52 is a known positive regulator of AR, GR and PR, and the direct targeting of FKBP52 would target the activity of all three receptors simultaneously.

Many factors (e.g. growth factors, cytokines, and angiogenic factors) implicated in prostate cancer progression are targets of the GR signaling pathway. GR signaling confers resistance to current antiandrogen treatments. Because data suggests that PR expression is elevated in metastatic disease, PR antagonists are therefore potential treatments for prostate cancer. Finally, based on data discussed below, targeting FKBP52 proline-rich loop interactions will abrogate β-catenin interaction with AR. Thus, the direct targeting of FKBP52 with small molecules will lead to a more potent drug with the potential to simultaneously hit a variety of targets known to have, or suspected of having, a role in prostate cancer.

MJC13 is described as an inhibitor of FKBP52-regulated AR activity (De Leon et. al. 2011. *PNAS*. 108(29): 11878-83) by targeting the AR BF3 surface. A novel mechanism is disclosed by which FKBP52 and β-catenin interact to co-regulate AR activity in prostate cancer cells. Data indicates that MJC13 targeting to the AR BF3 surface abrogates β-catenin interaction with AR. The FKBP52 proline-rich loop is critical for FKBP52/β-catenin co-regulation of AR activity, and that drugs that disrupt interactions at the proline-rich loop would effectively block FKBP52/β-catenin/AR interactions. Specific small molecules docked within the PPlase pocket affect proline-rich loop conformation and interactions. As illustrated in FIG. 1, FK506-binding to the FKBP12 PPlase pocket leads to a reorientation of the FKBP12 proline-rich loop. Thus, small molecules predicted to target the FKBP52 PPlase pocket have been identified in the disclosed embodiments.

I. Virtual Screening for FKBP52-Specific Inhibitors

The Binding Site: The most probable binding site is under the proline-rich loop, the PPlase binding site in FK1. Although the co-crystal of FKBP52 with ligands is still not available, the FKBP51-ligand crystal structure indirectly proved that this predicted site is the active site.

Figure 2:
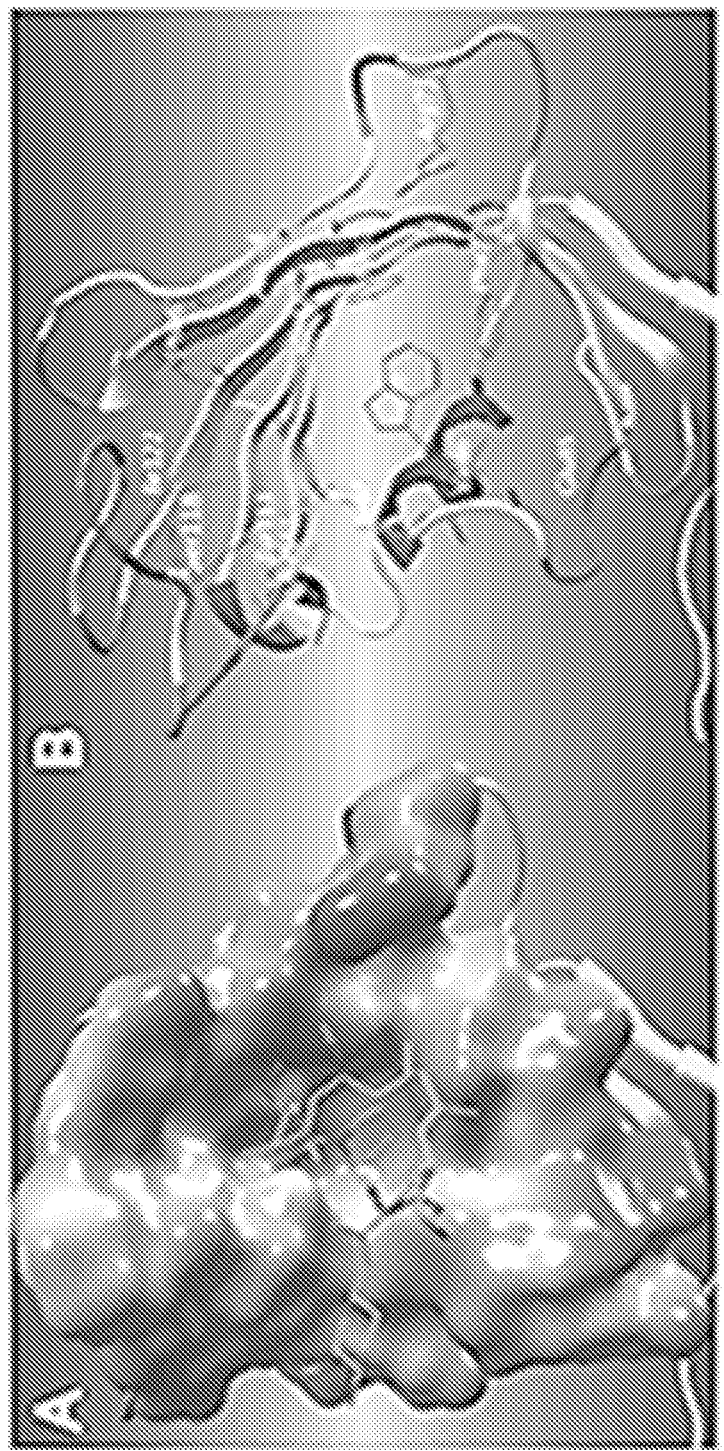
FIG. 2. FK506 docking in the FKBP52 PPlase pocket. (A) FKBP52 FK1 domain with FK506 docked in the PPlase pocket. (B) FKBP52 FK1 domain with PPlase pocket residues shown.

The Key Interactions: This binding site is highly hydrophobic, rich in hydrophobic residues, but only several polar residues. Structures of FKBP51/FKBP52 cocrystallized with small-molecules are not available. Therefore, the FKBP12 in complex with FK506 was used as a reference, illustrated in FIG. 2 herein, and found that hydrogen-bond interactions between the ligand and three residues Asp37, Ile56, and Tyr82, corresponding to Asp68, Ile87 and Tyr113 in FKBP52 are present, and that these key residues were retained in FKBP51-ligand cocrystal structure.

Virtual Screening Pipeline: The Zinc database was processed with 3 million lead-like compounds with two docking programs, Glide and eHiTs, using the glide score (SP<-5.5) and eHiTs score (eHiTs score<-1) as cutoffs to shrink the database (508,213 molecules left). RMSD values were calculated between the docked poses from these programs, and only molecules (8072 molecules) with consistent poses were retained (0<RMSD<2.5). Multiple scoring was then performed using different scoring functions (Pki, Xscore, ligx and glide xp), followed by consensus voting. To reduce false positive hits, both consensus voting and single scoring (sp and eHiTs) were used to select potential compounds. Compounds were then analyzed using a 3D visualization tool to remove those that do not retain key interactions.

Figure 3:
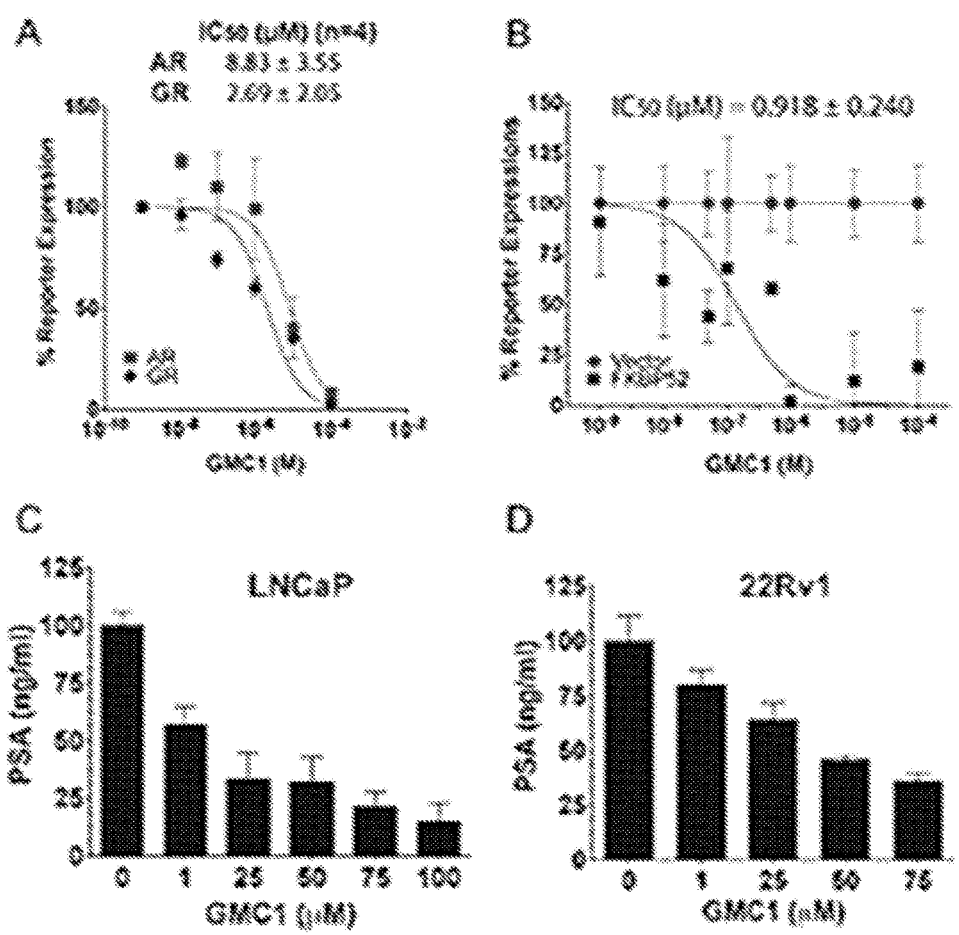
FIG. 3. The FKBP52-specific inhibitor GMC1 inhibits AR and GR activity. (A) Representative AR- and GR-mediated luciferase reporter assays in MDA-kb2 cells with a range of GMC1 concentrations. The average IC50 from 4 independent experiments are shown. (B) A representative luciferase reporter assay in 52KO mouse embryonic fibroblast cells in the presence or absence of FKBP52 were performed. Transfected cells were treated with DHT and a range of concentrations of GMC1 and assessed for AR-dependent expression of a luciferase reporter. The average IC50 of 3 independent assays is shown. (C-D) ELISA assays measuring androgen-dependent PSA secretion form LNCaP (C) and 22Rv1 (D) prostate cancer cells treated with the indicated concentrations of GMC1.
Figure 4:
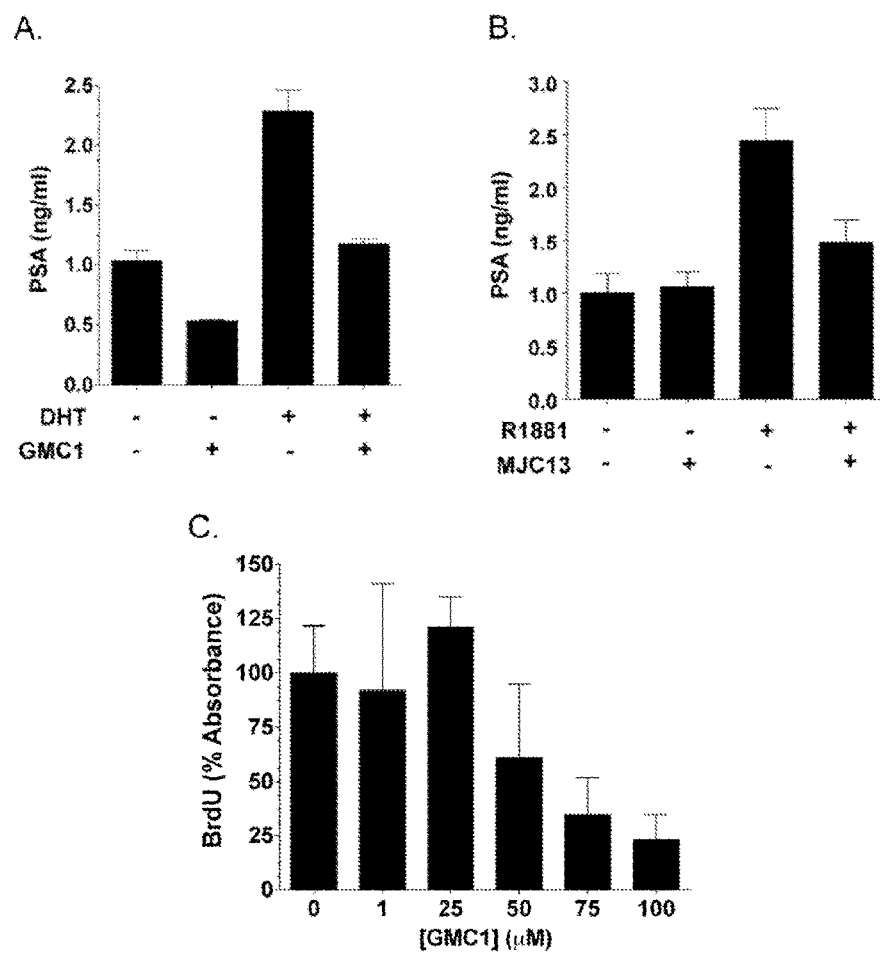
FIG. 4. GMC1 inhibits hormone-dependent and +independent PSA secretion and hormone dependent proliferation in 22Rv1 prostate cancer cells. (A) ELISA assay in 22Rv1 cells measuring GMC1 effects on PSA secretion in the presence and absence of hormone. (B) qPCR assay in 22Rv1 cells measuring endogenous PSA gene expression in the presence or absence of hormone. For comparison, GMC1, but not MJC13, inhibits hormone-independent PSA secretion and/or expression. (C) A BrdU incorporation assay was used to assess GMC1 effects on hormone-dependent 22Rv1 cell proliferation.
Figure 5:
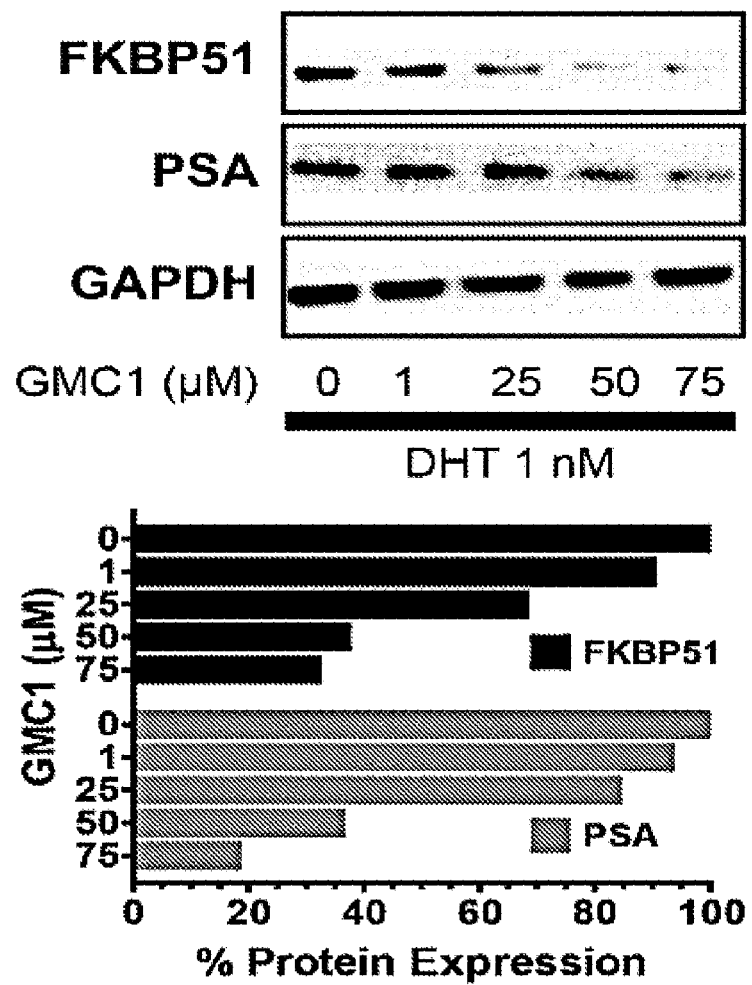
FIG. 5. Effects of GMC1 on AR-dependent gene expression in 22Rv1 prostate cancer cells. Western blots to measure AR-dependent expression of FKBP51 and PSA were performed in 22Rv1 cells. Cells were treated with the indicated concentrations of GMC1 in the presence of DHT for 24 hrs. Blots were probed with antibodies directed against FKBP51, PSA, and GAPDH as a loading control. The upper panel shows a representative Western blot. The lower panel depicts the representative densitometry data in which every value is normalized to the loading control and no drug treatment.

GMC1: A Lead Molecule with FKBP52-Specific Inhibition. Out of a total of 40 hits from the virtual screen, GMC1, 2-(1H-benzimidizol-2-ylsulfanyl)-N—[(Z)-(4methoxyphenyl)methylideneamino]acetamide was identified as the lead molecule with the most potent inhibition of AR-mediated reporter gene expression in MDA-kb2 cells (FIG. 3A). GMC1 produces a similar inhibition of GR-mediated reporter gene expression (FIG. 3A). As illustrated in FIG. 3B, GMC1 specifically inhibits FKBP52-regulated AR activity in 52KO MEF cells in the high nanomolar range. Preliminary ELISA assays demonstrate that GMC1 inhibits AR-dependent PSA expression in LNCaP (FIG. 3C) and 22Rv1 (FIG. 3D) prostate cancer cells at concentrations consistent with the effective concentrations in reporter assays.

Figures 6A, 6B:
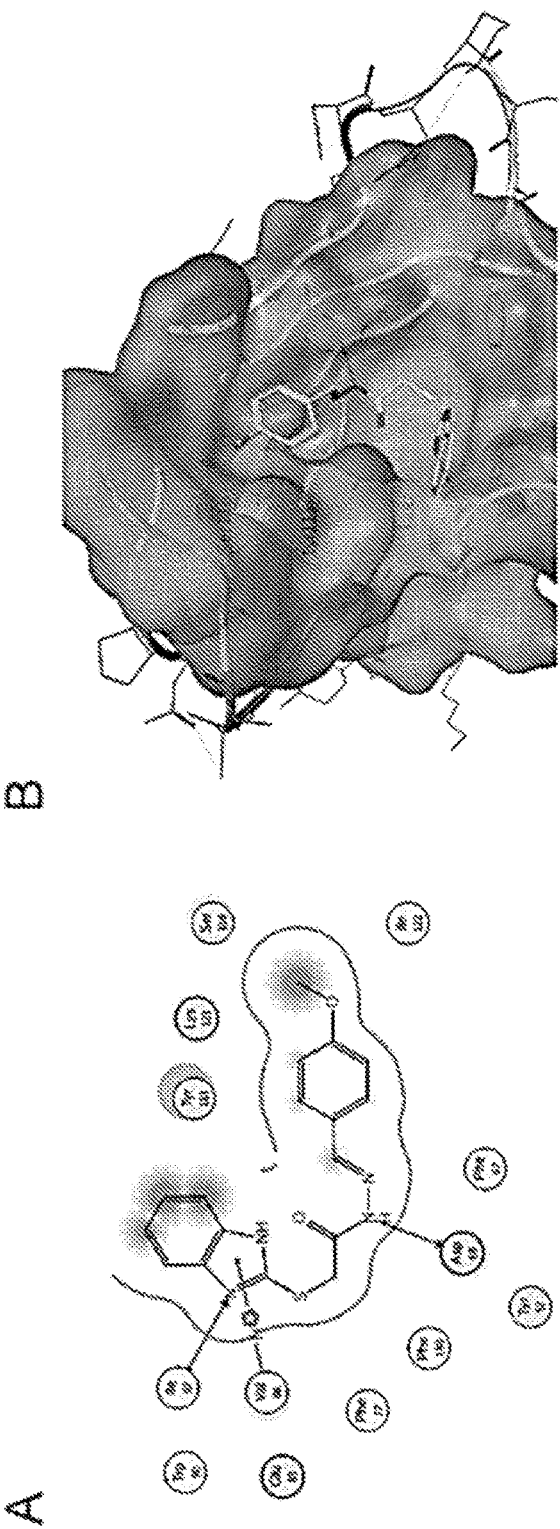
FIG. 6A-6B. GMC1/FKBP52 docking simulations. (A) A 2D image of GMC1 docked in the FKBP52 PPlase pocket showing predicted residue interactions. (B) A 3D image of GMC1 docked in the PPlase pocket.
Figure 7A:
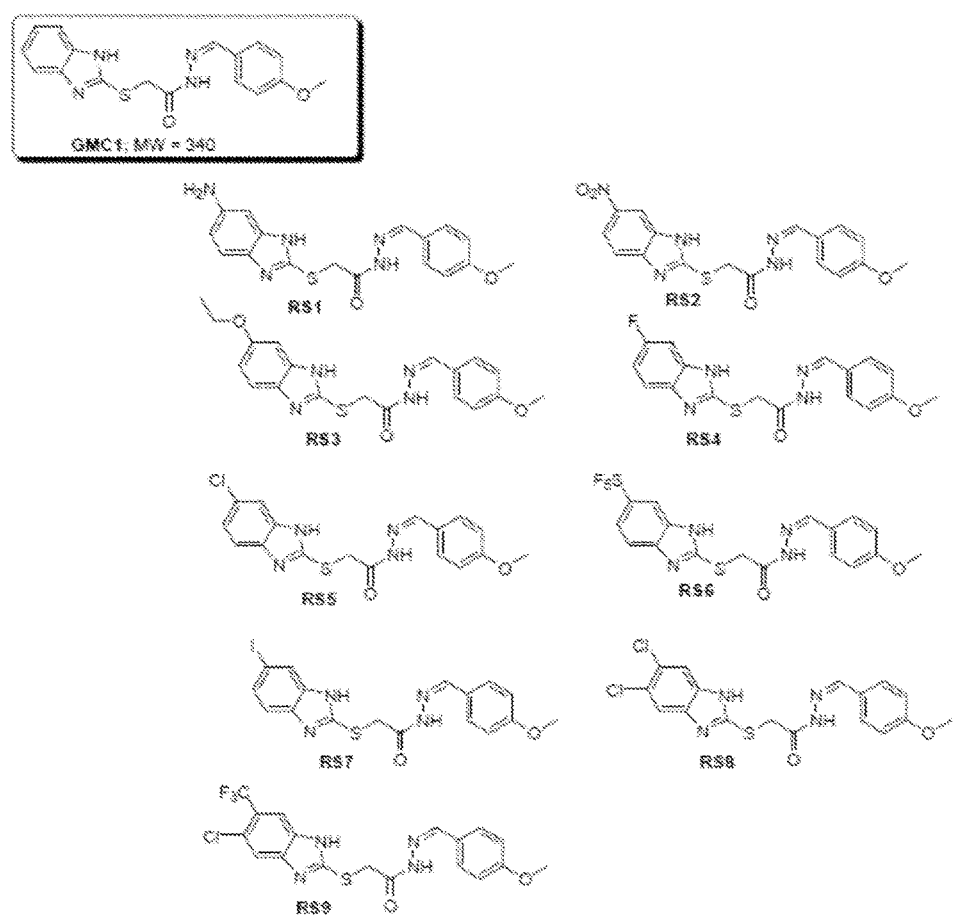
FIG. 7A-7L. GMC1 analogs.
Figure 7B:
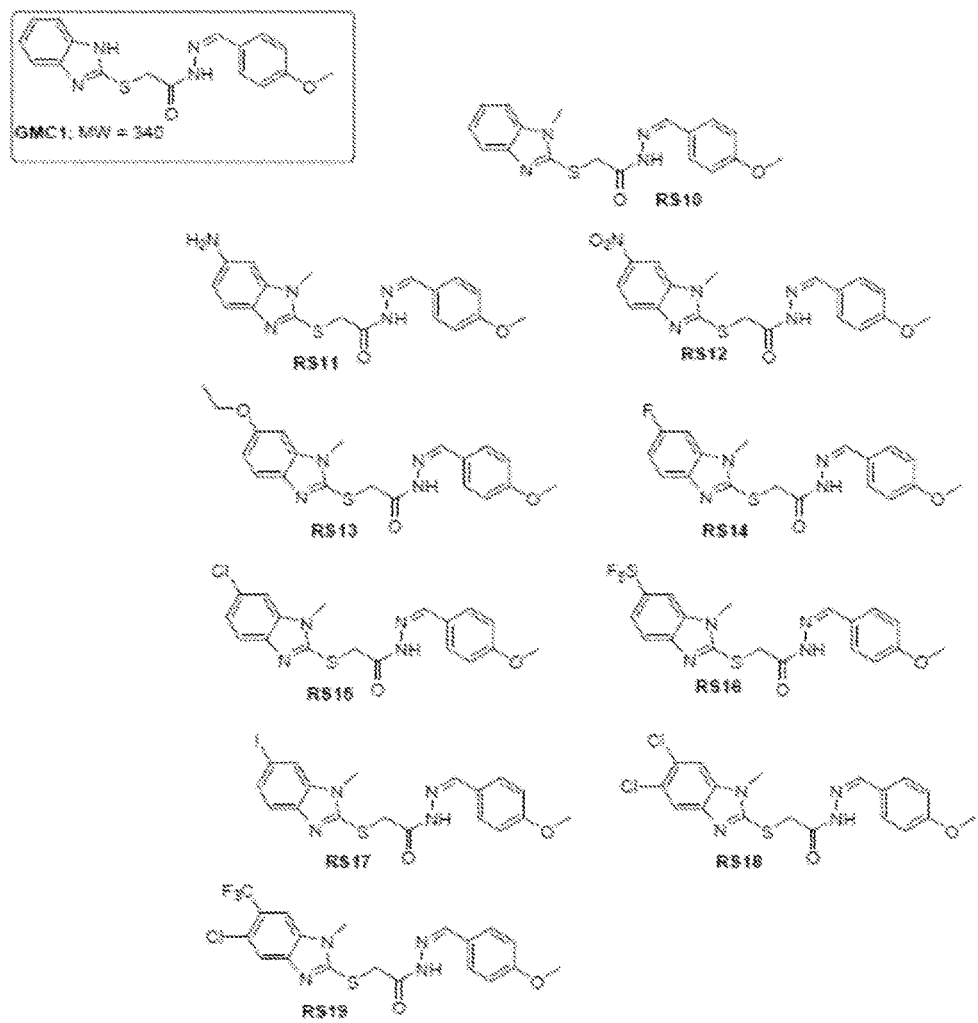
Figure 7C:
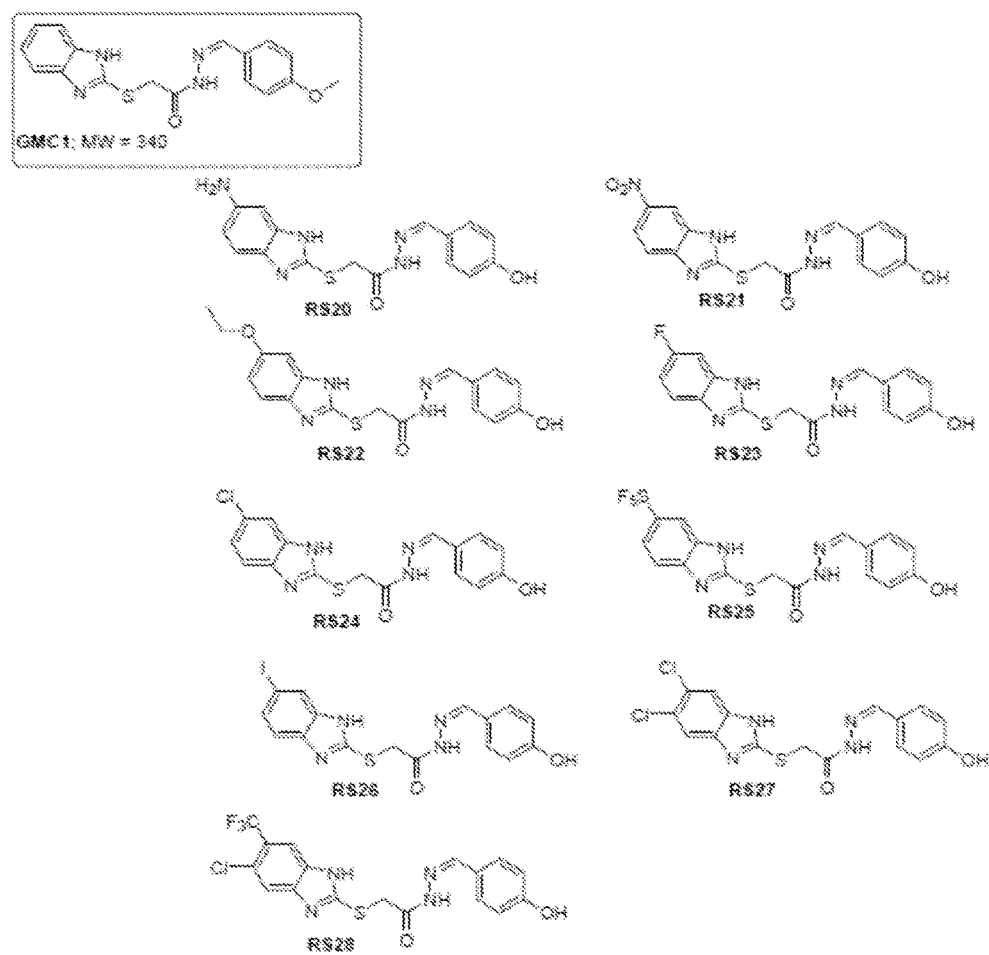
Figure 7D:
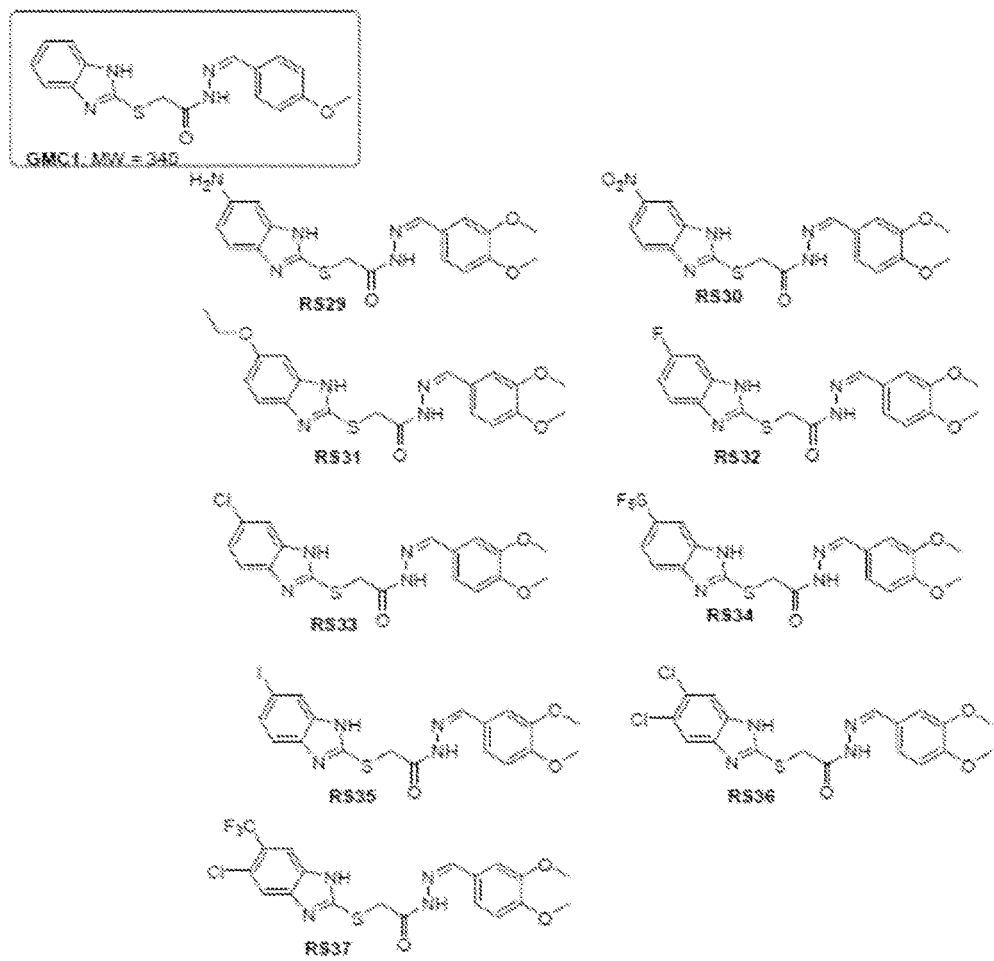
Figure 7E:
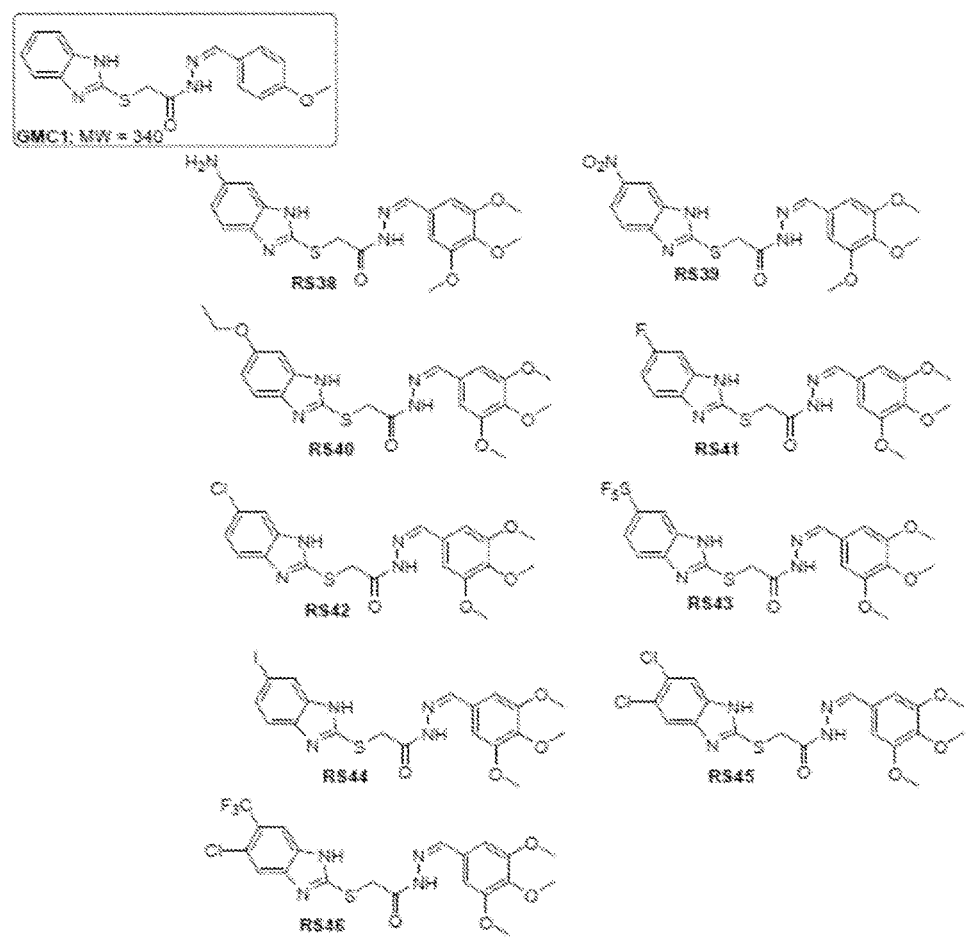
Figure 7F:
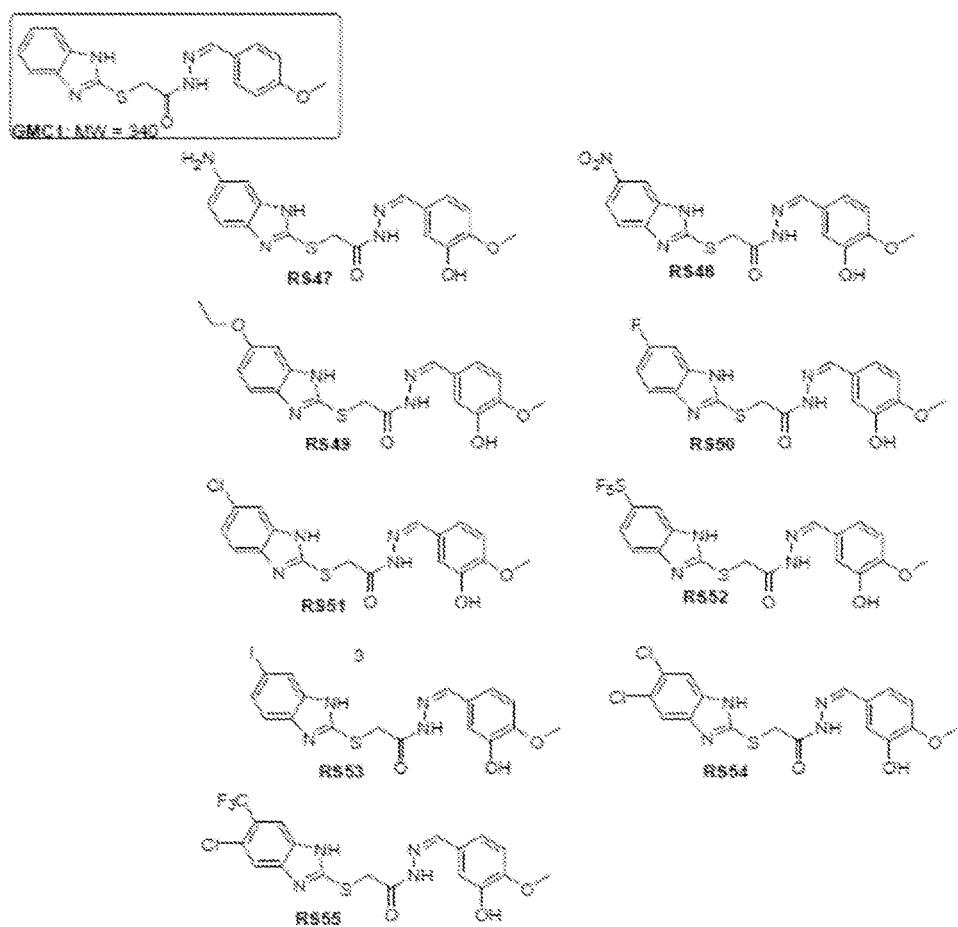
Figure 7G:
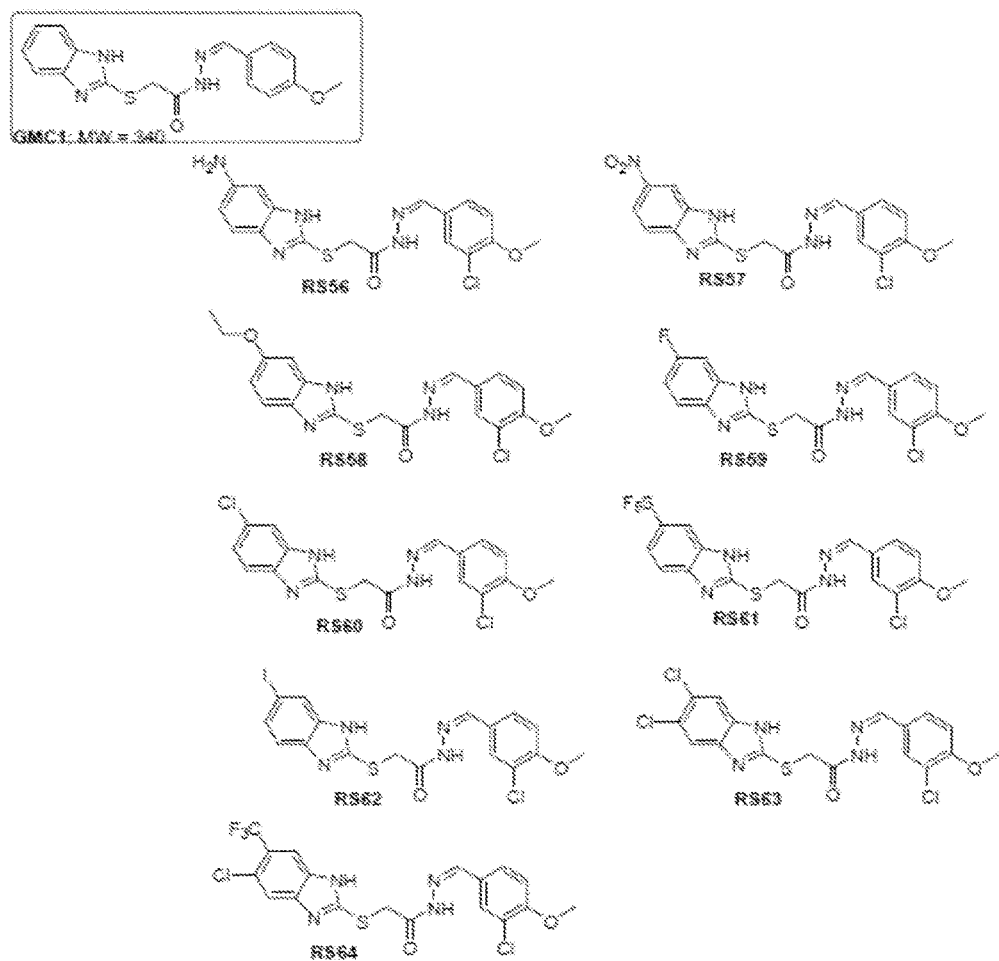
Figure 7H:
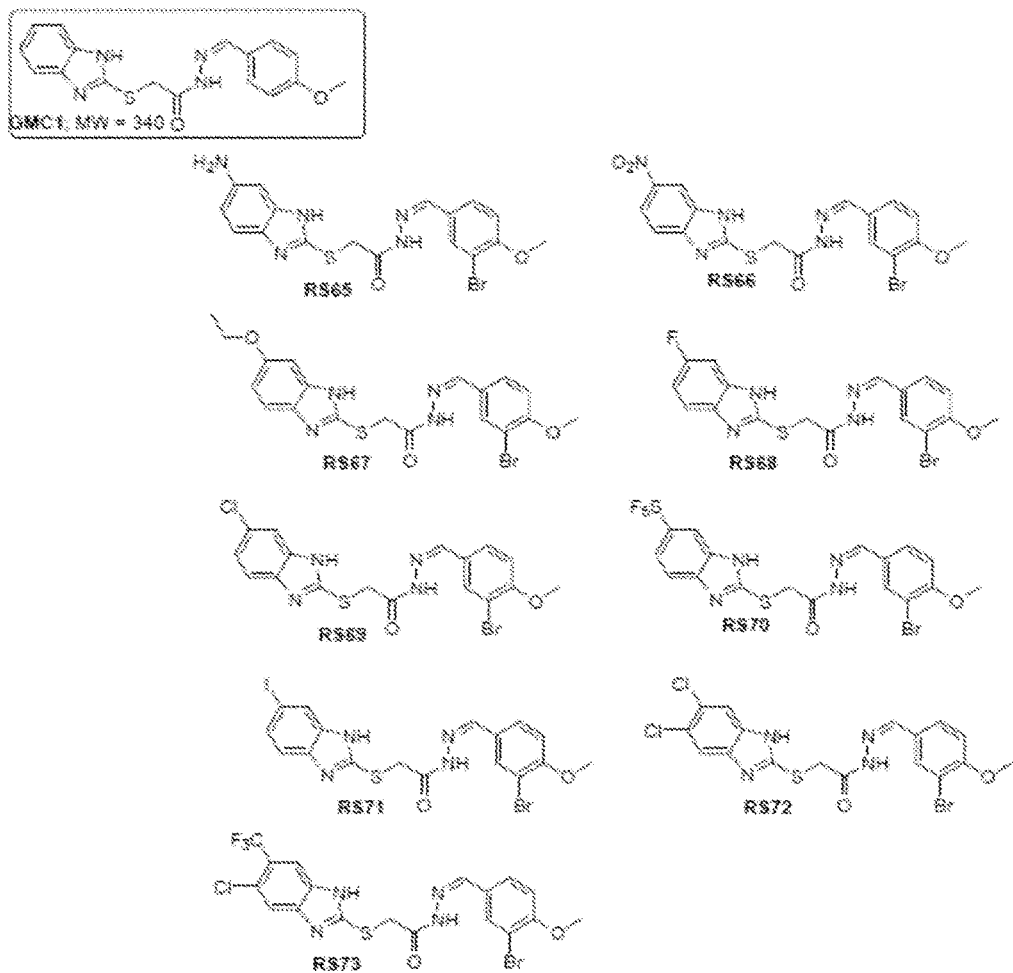
Figure 7I:
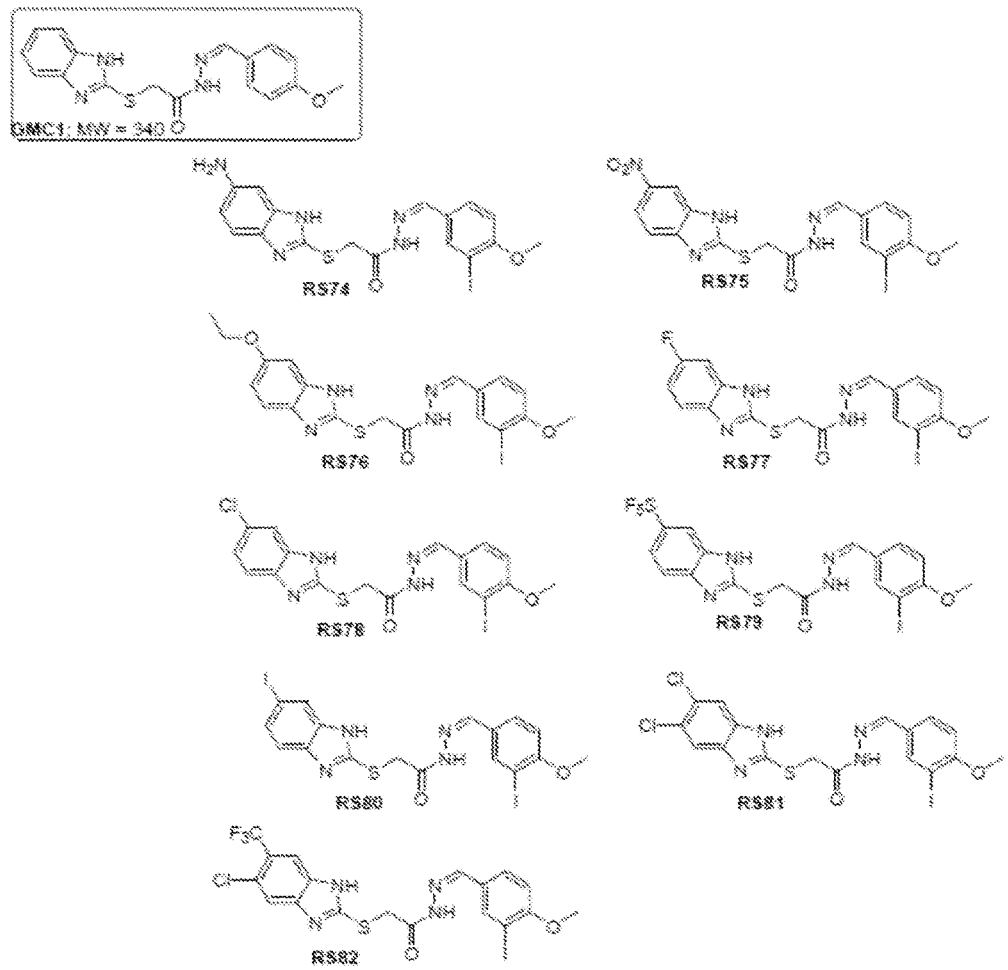
Figure 7J:
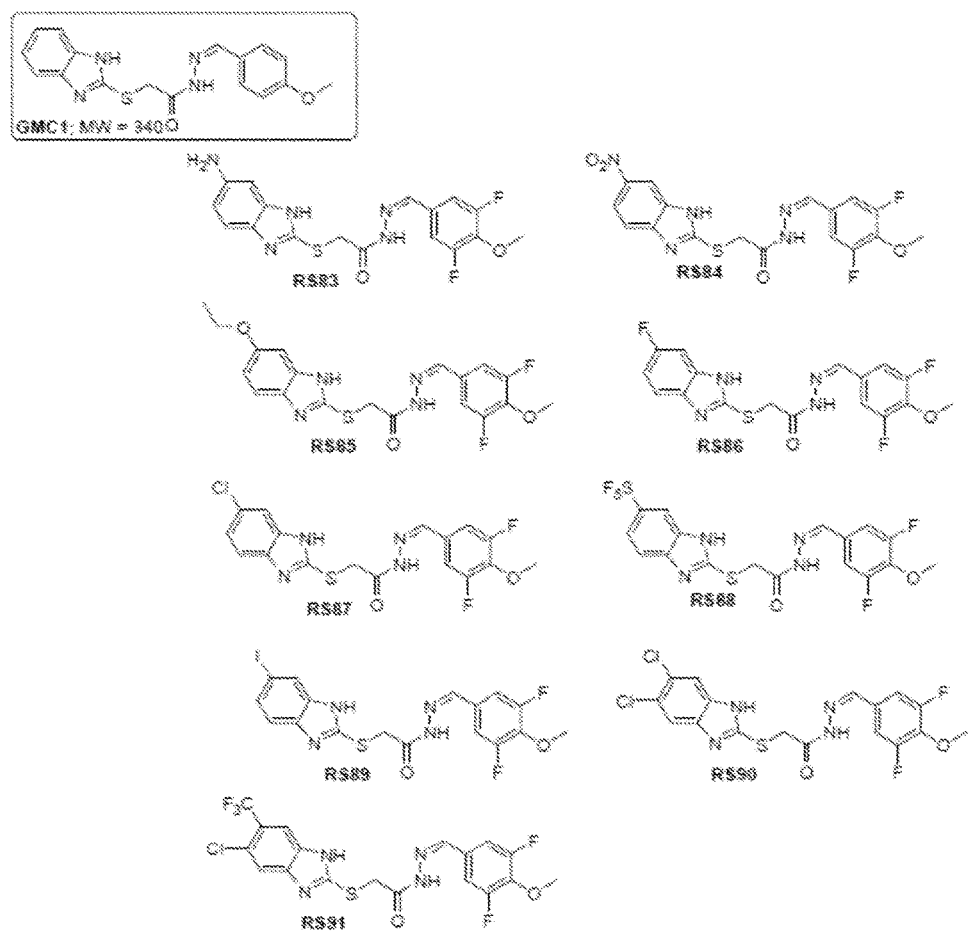
Figure 7K:
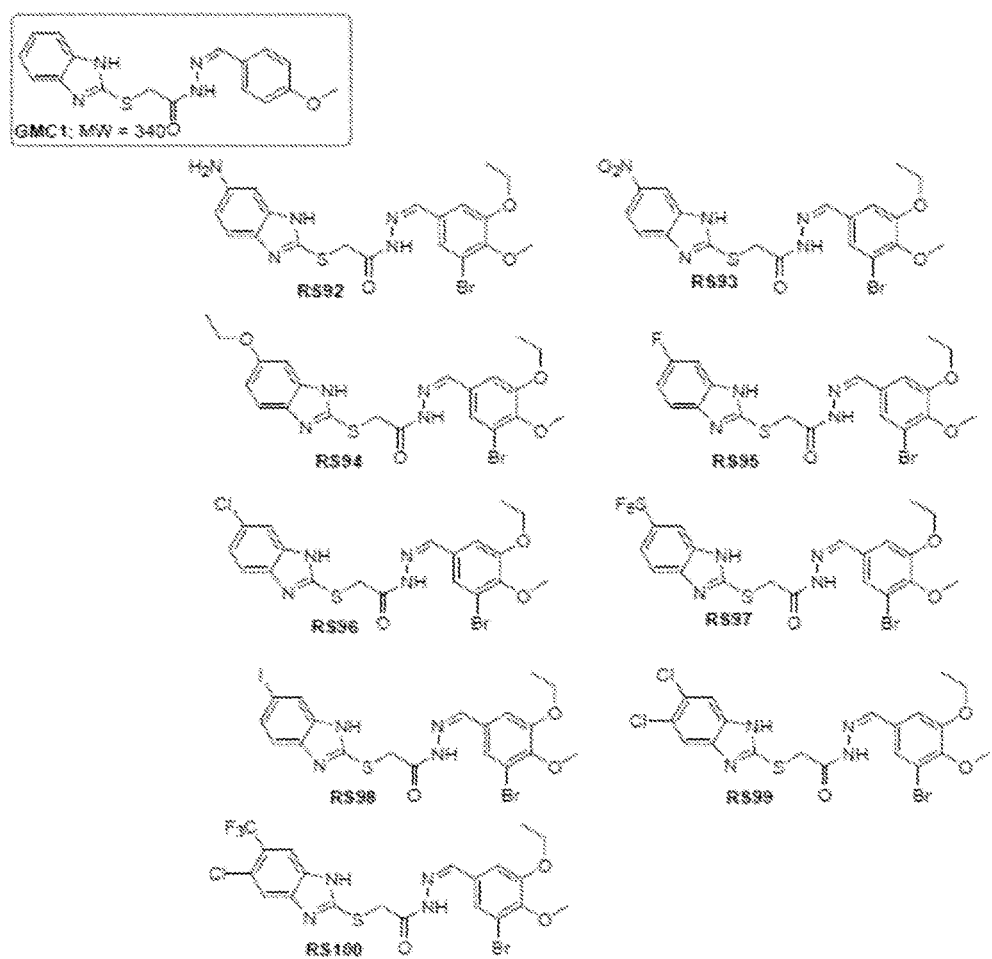
Figure 7L:
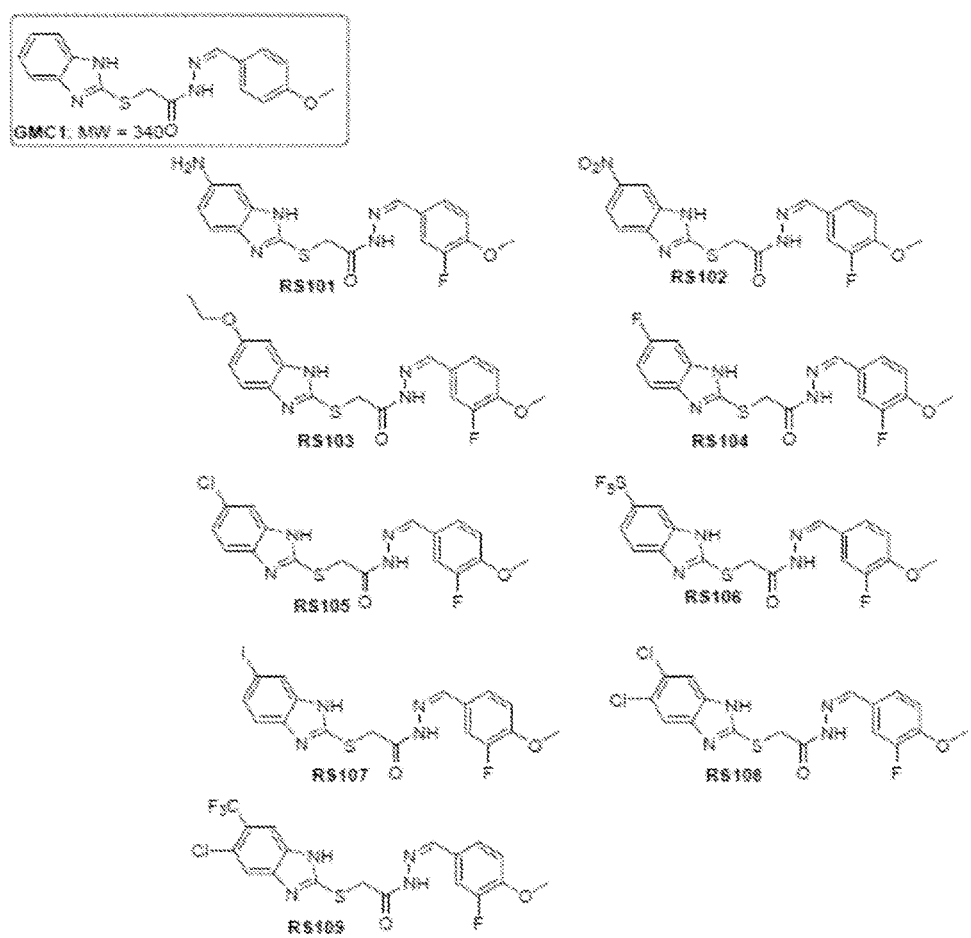

GMC1 represents a lead FKBP52-specific inhibitor that is predicted to bind within the FKBP52 PPlase pocket. Future studies will include fluorescence polarization assays to verify the drug binding site. As illustrated in FIG. 6, docking simulations are utilized to predict the drug binding site. The predicted drug-residue interactions shown in FIG. 6A can be assessed by testing FKBP52 point mutants that are predicted to lose drug binding.

Development of GMC1: The FKBP52 proline-rich loop that overhangs the PPlase pocket, but not the PPlase activity, is functionally critical for FKBP52 regulation of steroid hormone receptor signaling and for FKBP52/β-catenin co-regulation of AR activity. Specific molecules targeting the PPlase pocket will disrupt FKBP52 proline-rich loop interactions leading to the effective inhibition of AR, GR and PR signaling, prostate cancer cell proliferation, and prostate tumor formation.

Using structure-based drug design methodology and in silico library screening to identify small molecules targeting the FKBP52 PPlase pocket. The in silico screen and functional screening of 40 hits are completed. A lead molecule is identified and termed GMC1 that specifically inhibits FKBP52-regulated AR and GR activity in the high nanomolar range. Using GMC1 as the initial lead molecule, the PPlase target site is verified using fluorescence polarization and rationally design modifications for structure-activity relationship analysis to improve compound potency and solubility.

Evaluation of all Candidate Drug Compounds in Multiple Cellular Models of Prostate Cancer. These evaluations include drug effects on FKBP52 and receptor protein stability, receptor hormone binding, FKBP52 and receptor cellular localization, receptor-dependent gene expression, β-catenin interaction with AR, and prostate cancer cell proliferation.

Preclinical Evaluations in Murine Prostate Cancer Models. Lead compounds are tested for their ability to prevent tumor growth and reduce prostate tumor size in murine prostate cancer models, including prostate cancer xenografts using human prostate cancer cells in SCID mice.

II. GMC1 Analogs/Derivatives

Certain embodiments are directed to compositions and methods of use for a compound having a chemical structure of Formula II

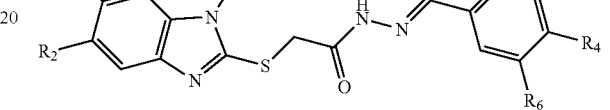

Formula II wherein $R_1$ or $R_2$ is independently and separately selected from H, amino, nitro, halogen, $F_5S$, $F_3C$, or C1-C3 alkoxy; $R_3$ is independently selected from H or C1-C3 alkyl; $R_4$ is independently selected from H, C1-C3 alkyl, C1-C3 alkoxy, or hydroxyl; $R_5$ is independently selected from H, halogen, or C1-C3 alkoxy; and $R_6$ is independently selected from H, halogen, hydroxyl, C1-C3 alkoxy. In certain aspects the halogen is F, Cl, or I.

Various chemical definitions related to such compounds are provided as follows.

As used herein, the term "water soluble" means that the compound dissolves in water at least to the extent of 0.010 mole/liter or is classified as soluble according to literature precedence.

As used herein, the term "nitro" means —$NO_2$; the term "halo" or "halogen" designates —F, —Cl, —Br, or —I; the term "mercapto" means —SH; the term "cyano" means —CN; the term "azido" means —$N_3$; the term "silyl" means —$SiH_3$, and the term "hydroxyl" means —OH.

The term "alkyl," by itself or as part of another substituent, means, unless otherwise stated, a linear (i.e. unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkenyl). The groups, —$CH_3$ (Me), —$CH_2CH_3$ (Et), —$CH_2CH_2CH_3$ (n-Pr), —$CH(CH_3)_2$ (iso-Pr), —$CH_2CH_2CH_2CH_3$ (n-Bu), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$ Si(CH$_3$)$_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents.

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means an oxygen that is double bonded to a carbon atom.

The term "alkylsulfonyl" as used herein means a moiety having the formula —S(O$_2$)—R', where R' is an alkyl group. R' may have a specified number of carbons (e.g. "C1 to C3 alkylsulfonyl" or "C$_{1-3}$ alkylsulfonyl")

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids, and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

Additional examples of pharmaceutically acceptable salts and their methods of preparation and use are presented in Handbook of Pharmaceutical Salts: Properties, Selection and Use (2002).

III. Methods for Treating

Described herein are methods and compositions related to treating or reducing the recurrence of hormone receptor dependent conditions, such as prostate cancer. Certain embodiments are directed to methods of treating the occurrence or reducing the recurrence of prostate cancer in a subject, comprising administering to the subject an effective amount of an agent that inhibits hormone receptors, directly or indirectly. In a further aspect, the methods include administering to the subject an effective amount of an agent that inhibits hormone receptors to inhibit or reduce proliferation of prostate cells or prostate cancer cells, wherein the subject is identified as having or is at risk for occurrence or recurrence of prostate cancer. In certain aspects the prostate cell is a prostate epithelial cell.

Prostate cancer is a proliferative disorder characterized by abnormal cell growth that originates in the prostate gland. A proliferative disorder refers to any cellular disorder in which the cells proliferate more rapidly than normal tissue growth. A proliferative disorder includes, but is not limited to, neoplasms, which are also referred to as tumors. Prostate cancer tumors can be adenocarcinomas of epithelial origin. Prostate cancer tumors can comprise prostate luminal epithelial cells, prostate basal epithelial cells, stromal cells, or a combination of prostate luminal epithelial, prostate basal epithelial cells or stromal cells. Prostate cancer tumors can comprise CK8+ prostate luminal epithelial cells. Prostate cancer tumors can also comprise CK5+ prostate basal epithelial cells which are also known as stem/progenital/basal epithelial cells.

As used herein, treating prostate cancer includes preventing, precluding, delaying, averting, obviating, forestalling, stopping, or hindering the onset, incidence, or severity of prostate cancer or the recurrence of prostate cancer in a subject. As utilized herein, by recurrence of prostate cancer is meant the reappearance of one or more clinical symptoms of prostate cancer after a period devoid of one or more clinical symptoms of prostate cancer. The disclosed method is considered to reduce the occurrence or recurrence of prostate cancer if there is a reduction or delay in onset, incidence or severity of the reappearance of prostate cancer, or one or more symptoms of prostate cancer (e.g., problems urinating, pain during urination, pelvic discomfort, swelling in the legs as a result of edema, blood in urine, swelling of the lymph glands, bone pain) in a subject at risk for occurrence or recurrence of prostate cancer. The disclosed method is also considered to reduce the recurrence of prostate cancer if there is a reduction or delay in onset, incidence or severity of the reappearance of prostate cancer, or one or more symptoms of prostate cancer (e.g., problems urinating, pain during urination, pelvic discomfort, swelling in the legs as a result of edema, blood in urine, swelling of the lymph glands, bone pain) in a subject at risk for recurrence of prostate cancer after receiving a prostate cancer therapy. Thus, the reduction or delay in onset, incidence or severity of recurrence of prostate cancer can be about a 10, 20, 30, 40, 50, 60, 70, 80, 90, 100%, or any amount of reduction in between.

As used throughout, by subject is meant an individual. Preferably, the subject is a mammal and, more preferably, a human. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Veterinary uses and formulations for same are also contemplated herein. A utilized herein, a subject at risk for recurrence of prostate cancer is a subject that is at risk for the reappearance of prostate cancer after treatment for prostate cancer or after remission from prostate cancer.

Treatment methods for prostate cancer include, but are not limited to, orchiectomy (surgical castration), prostatectomy, anti-androgen therapy (for example, Eulexin®, Casodex®, Nilandron® and Nizoral®), radiation therapy, chemotherapy, luteinizing hormone releasing hormone analogs (for example, Lupron®, Viadur®, Eligard®, Zoladex®, Trelstar® and Vantas®), lutenizing hormone releasing hormone antagonists (for example, Plenaxis® and) Firmagon® or combinations of these treatment methods. After treatment, a subject can be monitored for recurrence of prostate cancer. Routine follow up visits after treatment allow one of skill in the art to determine if the subject is devoid of clinical symptoms or if clinical symptoms of prostate cancer have reappeared. In order to determine the status of the subject, a blood test to measure PSA levels can be performed. The results of the PSA test can indicate that prostate cancer can or has recurred. Imaging techniques, such as X-rays, MRIs, CT scans and bone scans can also be used. Lymph node examinations, biopsies, and digital rectal examinations can also be utilized to identify a subject at risk for recurrence of prostate cancer. These techniques can also be used to stage any recurrence of prostate cancer.

Also provided is a method of treating prostate cancer in a subject, comprising selecting a subject with prostate cancer and administering to the subject an effective amount of an agent described herein.

Further provided is a method of reducing prostate tumor progression in a subject, comprising administering to the subject an effective amount of an agent described herein. This method can be performed in combination with antiandrogen therapy that decreases proliferation of prostate luminal epithelial cells and/or stromal cells or independent of anti-androgen therapy.

As utilized herein, by reducing prostate tumor progression is meant a method of preventing, precluding, delaying, averting, obviating, forestalling, stopping, or hindering prostate tumor progression in a subject. The disclosed method is considered to reduce prostate tumor progression if there is a reduction or delay in prostate tumor growth, metastasis, or one or more symptoms of prostate cancer (e.g., problems urinating, pain during urination, pelvic discomfort, swelling in the legs as a result of edema, blood in urine, swelling of the lymph glands, bone pain) in a subject with a prostate tumor. The disclosed method is also considered to reduce prostate tumor progression if there is a reduction or delay in prostate tumor growth, metastasis or one or more symptoms of prostate cancer (e.g., problems urinating, pain during urination, pelvic discomfort, swelling in the legs as a result of edema, blood in urine, swelling of the lymph glands, bone pain) in a subject with a prostate tumor after receiving an agent described herein as compared to the subject's progression prior to receiving treatment. Thus, the reduction or delay prostate tumor can be about a 10, 20, 30, 40, 50, 60, 70, 80, 90, 100%, or any amount of reduction in between.

The agents described herein can be provided in a pharmaceutical composition. Depending on the intended mode of administration, the pharmaceutical composition can be in the form of solid, semi-solid, or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, or other material well known in the art for use in pharmaceutical formulations. The choice of a carrier for use in a composition will depend upon the intended route of administration for the composition. The preparation of pharmaceutically acceptable carriers and formulations containing these materials is described in, for example, Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; saltforming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Administration can be carried out using therapeutically effective amounts of the agents described herein for periods of time effective to treat or reduce recurrence of prostate cancer or other hormone receptor associated conditions. The effective amount may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the activity of the specific compound employed, the metabolic stability and length of action of that compound, the species, age, body weight, general health, sex and diet of the subject, the mode and time of administration, rate of excretion, drug combination, and severity of the particular condition and can be determined by one of skill in the art. The dosage can be adjusted by the physician as needed, e.g., in the event of any contraindications. Dosages can vary, and can be administered in one or more dose administrations daily, for one or several days. Guidance can be found in the literature for appropriate dosages for given classes of pharmaceutical products.

Any appropriate route of administration may be employed, for example, parenteral, intravenous, subcutaneous, intramuscular, intraventricular, intracorporeal, intraperitoneal, rectal, or oral administration. Administration can be systemic or local. Pharmaceutical compositions can be delivered locally to the area in need of treatment, for example by topical application or local injection. Multiple administrations and/or dosages can also be used. Effective doses can be extrapolated from dose-response curves derived from in vitro or animal model test systems.

The disclosure also provides a pharmaceutical pack or kit comprising one or more containers filled with one or more of the ingredients of the pharmaceutical compositions. Instructions for use of the composition can also be included.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules included in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

The invention claimed is:

1. An FKBP52 binding molecule having a chemical structure of Formula II

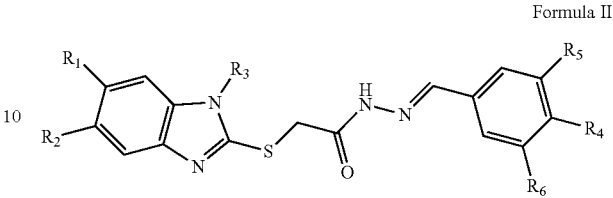

Formula II wherein $R_1$ or $R_2$ are independently and separately selected from H, amino, nitro, halogen, $F_5S$, $F_3C$, or C1-C3 alkoxy, wherein $R_1$ and $R_2$ are not both H; $R_3$ is independently selected from H or C1-C3 alkyl; $R_4$ is independently selected from H, C1-C3 alkyl, C1-C3 alkoxy, or hydroxyl; $R_5$ is independently selected from H, halogen, or C1-C3 alkoxy; and $R_6$ is independently selected from H, halogen, hydroxyl, and C1-C3 alkoxy, wherein $R_6$ is not C1 alkoxy, when $R_1$ or $R_2$ is chlorine, $R_4$ is C1 alkoxy and $R_5$ is hydrogen; and $R_5$ is not C1 alkoxy when $R_1$ or $R_2$ is chlorine, $R_4$ is C1 alkoxy, and $R_6$ is hydrogen.

2. The molecule of claim 1, wherein $R_1$, $R_2$, $R_5$, or $R_6$ is independently selected from H, F, Cl, or I.

3. The molecule of claim 1, wherein $R_1$, $R_2$, $R_5$, or $R_6$ is independently F.

4. A method of treating prostate cancer comprising administering an effective amount of the compound of claim 1 to a subject having prostate cancer.

* * * * *